United States Patent [19]
Bokros et al.

[11] Patent Number: 5,236,449
[45] Date of Patent: Aug. 17, 1993

[54] HEART VALVE PROSTHESES

[75] Inventors: Jack C. Bokros; Michael R. Emken, both of Austin; Axel D. Haubold, Liberty Hill; T. Scott Peters, Georgetown; Jonathan C. Stupka, Austin, all of Tex.

[73] Assignee: Onx, Inc., Austin, Tex.

[21] Appl. No.: 888,872

[22] Filed: May 26, 1992

Related U.S. Application Data

[63] Continuation-in-part of Ser. No. 730,126, Jul. 15, 1991, Pat. No. 5,137,532.

[51] Int. Cl.⁵ .............................................. A61F 2/24
[52] U.S. Cl. ......................................................... 623/2
[58] Field of Search .............................................. 623/2

[56] References Cited

U.S. PATENT DOCUMENTS

| | | | |
|---|---|---|---|
| 4,272,854 | 6/1981 | Bokros | 623/2 |
| 4,308,624 | 1/1982 | Klawitter | 623/2 |
| 4,328,592 | 5/1982 | Klawitter | 623/2 |
| 4,357,715 | 11/1982 | Klawitter | 623/2 |
| 4,373,216 | 2/1983 | Klawitter | 623/2 |
| 4,443,894 | 4/1984 | Klawitter | 623/2 |
| 4,451,937 | 6/1984 | Klawitter | 623/2 |
| 4,692,165 | 9/1987 | Bokros | 623/2 |
| 4,863,458 | 9/1989 | Bokros | 623/2 |

Primary Examiner—David Isabella
Assistant Examiner—Dinh X. Nguyen
Attorney, Agent, or Firm—Fitch, Even, Tabin & Flannery

[57] ABSTRACT

Prosthetic heart valves having a single occluder, or a pair of identical mating occluders, guided in their movement from the open to the closed position by pairs of elongated slots in diametrically opposed flat sidewall sections of the valve body. Each occluder is formed with two ears that protrude from opposite flat side surfaces along the lateral edges thereof. The ears may be frustoconical or hemispherical or the like and are slidingly received in elongated slots which can be straight or arcuate. The main body portions of the occluders have rectilinear surfaces that are aligned parallel to the centerline through the valve in the open position, so as to give low resistance to blood flow. However, when the backflow of blood displaces the occluders upstream, the slot arrangements are such that even though the occluder bodies are parallel, pivoting towards the closed position orientation begins essentially immediately, and the closing movement is of short duration so as to minimize regurgitation.

20 Claims, 3 Drawing Sheets

0
HEART VALVE PROSTHESES

FIELD OF THE INVENTION

This application is a continuation-in-part of our earlier application U.S. Ser. No. 730,126 filed Jul. 15, 1991, now U.S. Pat. No. 5,137,532.

The present invention relates to mechanical heart valve prostheses and, in particular, to improved prosthetic heart valves having valve members or occluders which both pivot and translate in moving between the open and closed positions.

BACKGROUND OF THE INVENTION

A wide variety of heart valve prostheses have been developed to operate hemodynamically, in conjunction with the pumping action of the heart, to take the place of defective natural valves. These valves variously have valve bodies which are designed to function either with valve members in the form of a single occluder or in the form of a pair of occluders or leaflets, which valve members pivot along eccentric axes (or both pivot and translate) to open and close a central blood flow passageway through the valve body.

U.S. Pat. No. 4,272,854 (Jun. 16, 1981) shows an early version of a bi-leaflet heart valve having an ear extending from each lateral side of each leaflet, which ear pivots in a recess, guided in part by a knob traveling in a longitudinal slot that is cut more deeply into the sidewall of the valve body.

U.S. Pat. No. 4,373,216 (Feb. 15, 1983) discloses both single occluder and bi-leaflet heart valves wherein protrusions, extending generally radially inward from a pair of flat sidewall sections of the valve body, guide valve members which have slots in their lateral edges to receive such protrusions.

Figures 3, 4:
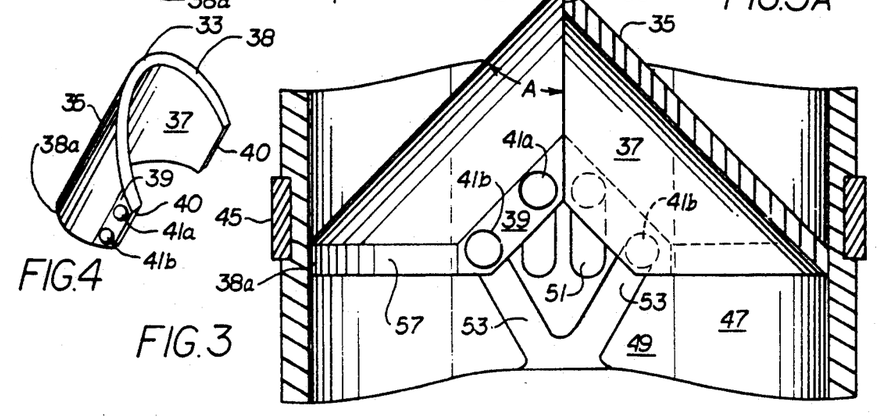
FIG. 3 is a cross-sectional view of the heart valve of FIG. 1 shown with the occluders in the closed position with the left-hand occluder again shown in elevation.
FIG. 4 is a perspective view of one of the occluders depicted in the heart valve of FIG. 2.

U.S. Pat. No. 4,308,624 (Jan. 5, 1982) discloses heart valves of both the single occluder and bi-leaflet type having curved valve members which both rotate and translate in moving between the open and closed positions. Although the leaflets are intended to be able to assume a parallel orientation in the open position, as shown in FIG. 3, study of the valve arrangement shows that, upon reversal of blood flow through the passageway, the leaflets could translate upstream without beginning to rotate toward the closed position. Although pivoting could occur in the intended manner, once the leaflets have moved upstream (having been guided by the paths the spherical ears trace in the slots 21), one or both of the leaflets might possibly counterrotate, depending upon the instantaneous attitude of bloodstream flow, and thereby not close on that stroke. U.S. Pat. Nos. 4,328,592 and 4,443,894 (Apr. 24, 1984) disclose later versions of this valve. The latter illustrates an embodiment wherein the leaflets in their open position are angled relative to the centerline plane (see Column 4, lines 39-43) so that, when flow reversal occurs (as depicted in FIG. 4), the alignment of angled surfaces 44 of the stops 41 and the placement of the stops is such that inward pivoting or counterrotation of the leaflets is precluded (see Column 5, lines 34-41).

U.S. Pat. No. 4,357,715 shows another embodiment of a heart valve of this general type which has an elongated depression within each slot in the valve sidewall to permit only controlled lateral movement within the slot.

U.S. Pat. No. 4,451,937 (Jun. 5, 1984) shows additional single occluder and bi-leaflet valves wherein valve members are oriented at an angle to the centerline plane in the open position; they pivot and translate to their closed positions guided, in part, by laterally extending ears 21 that move in generally arcuate slots or depressions 23.

U.S. Pat. No. 4,692,165 (Sept. 8, 1987) discloses single occluder and bi-leaflet valves wherein valve members have notches in their lateral edges which receive arcuate posts protruding from flat sidewall sections of the valve body; the posts guide the pivotal and translational movement of the valve members.

U.S. Pat. No. 4,863,458 (Sept. 5, 1989) discloses bi-leaflet heart valves having valve members of varying thickness which are guided in generally pivotal movement by laterally extending ears that are received in recesses formed in the flat sidewall sections of the valve bodies.

Commercially developed heart valves, using valve members of the type very generally exemplified by some of the above-mentioned U.S. patents, have employed those valve members oriented at an angle to the centerline plane in the open position, so that the backflow of blood preferentially impinges upon the outflow surfaces of each valve member and thus initially imparts a pivotal force component in the direction of its closing movement. It is now felt to be particularly important that a mechanical heart valve prosthesis should provide a passageway through which blood can flow freely in the open position with a minimum of drag. To accomplish this desired objective, it is now believed that the valve members should be able to assume an orientation which is parallel to the longitudinal axis of the passageway; however, in such orientation, it is important that the valve members should still be highly responsive to backflow so as to close quickly with a minimum of regurgitation. Improvements in valve construction have continued to be sought with the objective of creating mechanical valves having such characteristics.

SUMMARY OF THE INVENTION

The present invention provides mechanical heart valve prostheses having the aforementioned desirable characteristics wherein a valve member or members can assume an open position parallel to the longitudinal axis of the valve passageway, but will promptly translate and begin to pivot toward its closed position orientation as soon as upstream displacement of such valve member occurs within the valve body. These valves include a pivot arrangement wherein pairs of first and second elongated slots are located in two diametrically opposed flat sidewall sections of the valve body, with two such pairs being provided for each valve member. First and second ears protrude from opposite lateral surfaces of each valve member and are slidably received in elongated slots. The pairs of slots are so positioned that, when backflow of blood creates drag forces upon the surfaces of the valve members and displaces the valve members upstream, engagement of the first and second ears against the walls of the first and second slots is such that each valve member quickly begins to pivot as it translates upstream.

This arrangement assures that a valve member, even when it is in an open position oriented precisely parallel to the valve centerline at the instant of the beginning of backflow, will promptly begin to pivot or swing toward its closed position orientation, thus assuring efficient, positive closing action. This desirable positive closing action is created without the need for any additional interengaging elements on the valve body or on the valve members, which provides a particularly clean construction at the interior of the valve body so that the interior sidewall of the valve body can be a purely cylindrical surface except for the two flat diametrically opposed wall sections. Likewise, the valve members can be made so that their major surfaces, which will be in the path of the blood flow, are essentially totally rectilinear because the ears will be received in the elongated slots and are therefore located out of the major path of the flowing bloodstream. The slot orientations and shapes of these valve pivot arrangements can be arranged to create a generally soft, final closing movement, and the load on the valve members at the instant of closing can be distributed such as to assure a tight seal is achieved between abutting, mating edge surfaces of two leaflets.

DETAILED DESCRIPTION OF THE PREFERRED EMBODIMENTS

Figures 1, 2, 3A, 5:
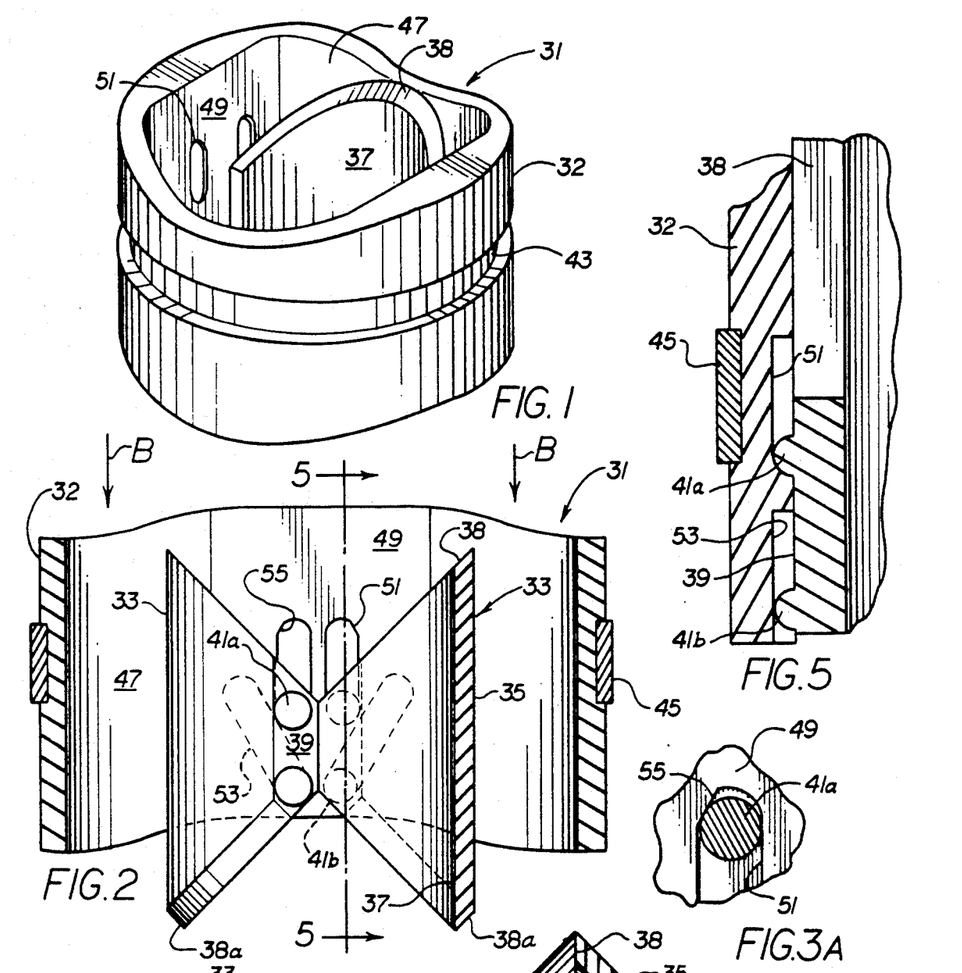
FIG. 1 is a perspective view of a bi-leaflet heart valve embodying various features of the present invention wherein the valve body is shown with only one of the two occluders installed.
FIG. 2 is a cross-sectional view, enlarged in size, of the heart valve of FIG. 1 with both occluders installed and shown in the open position, but with the left-hand occluder shown in elevation.
FIG. 3A is an enlarged fragmentary view of the ear in the left-hand slot of the valve as shown in FIG. 3.
FIG. 5 is an enlarged fragmentary, sectional view taken generally along the line 5—5 of FIG. 2.

Shown in FIGS. 1-5 is a bi-leaflet heart valve 31 which incorporates an elongated valve body 32 and a pair of curved leaflets 33. Each of the pair of leaflets 33 has a convex inflow surface 35 and a concave outflow surface 37. These rectilinear surfaces form the main body portion of the leaflet which has a sidewall of uniform thickness except for the two regions along the lateral edges where there is a slight thickening to create a pair of flat lateral surface sections 39 which lie adjacent to short straight lateral edge surfaces 40. A pair of ears or bosses 41 protrude from each lateral surface section 39 and coact to define the pivoting-sliding motion of the leaflets. In essence, therefore, each leaflet 33 is generally a section of a tube or hollow cylinder of elliptical or oval cross-section, except for the flat lateral surfaces 39, as perhaps best seen in FIG. 4, and each leaflet has a flat upstream mating edge 38 and a downstream arcuate edge 38a. A pivot mechanism allows the leaflets 33 to assume an orientation in the open position with their rectilinear surfaces parallel to the centerline of the valve and thus substantially parallel to the flow of blood through the valve. As a result of its construction, as shown in FIG. 2, the valve 31 has an enlarged central flow channel in its open position, compared to a valve having two flat leaflets such as that described hereinafter.

The valve body 32 is elongated in axial length, preferably having an axial dimension equal to about 60 percent of the effective internal diameter of the passageway through the valve body. The valve body 32 is slightly scalloped, both top and bottom, so as to have a substantially uniform height or length about its entire 360° periphery. However, as best seen in FIG. 2, the valve body includes an upstream extension in each region of the flat sidewall section 49 and a similarly shaped downstream depression or cutout in the same two regions. The annular valve body 32 has a shape which is essentially that of a hollow right circular cylinder, having a groove 43 in its exterior surface designed to accommodate a metal stiffening ring 45. The stiffening ring 45, shown installed in FIGS. 2, 3 and 5, is used for the attachment of a standard sewing ring (not shown) to the valve as well known in this art. An otherwise cylindrical interior sidewall surface 47 of the valve body 32 is interrupted by a pair of diametrically opposed flat wall sections 49; however, all interior surfaces are smooth and parallel to the centerline through the valve body. The proportioning of the leaflets 33 is such that the flat side sections 39 of the leaflets are located in essentially sliding contact with the flat interior wall sections 49 of the valve body, thus providing both bearing surfaces and seals in these regions.

Two pairs of relatively shallow elongated slots 51, 53 having generally parallel sidewalls are located in each of the flat wall sections, which slots receive the ears 41 on the leaflets and coact therewith to define the movement of the leaflets between the open and closed positions. As best seen perhaps in FIG. 5, the ears 41 which project from the side sections 39 of the leaflets are spheroidal in shape, being illustrated as nearly hemispheres, and their curvature is generally matched with the cross sectional radius of curvature of the shallow slots 51 and 53. The slots have a slightly greater radius of curvature to assure there will be smooth movement of the ears within the slots. The lengths of the slots should be such so that the ears can translate a distance equal to at least about their diameter. The ears 41 have surfaces which are curved in two perpendicular planes; however, they can have other suitable curved shapes, preferably curved in only one of two perpendicular planes, e.g. generally cylindrical or frustoconical, as discussed herein.

In the open position illustrated in FIG. 2 with normal blood flow through the valve being in the downstream direction indicated by the arrows B, the leaflets 33 are located at the downstream ends of both slots 51, 53. Although the leaflets are curved in profile, their main body surfaces are rectilinear, i.e. made up of a locus of straight lines, and because these surfaces are aligned parallel to the centerline of the valve in the open position, the leaflets provide minimal resistance to blood flow in the downstream direction. As soon as blood flow reverses, the leaflets 33 are displaced upstream, and the upstream translational movement of the spherical ears 41 is guided by the orientation of the pairs of slots 51, 53.

As can be seen in FIGS. 2 and 3, the upstream slots 51 of each pair are straight and oriented parallel to the centerline of the valve passageway. The downstream slots 53 of each pair are also straight, but are oriented at an upstream angle (the angle taken facing upstream) of about 35° to the orientation of the upstream slots and also to the valve centerline plane; the angle is generally between about 25° and about 45°. By centerline plane is meant the plane perpendicular to the flat sidewall sections 49 which contains the valve body centerline. In other words, the orientation is such that the upstream portions of the slots 51, 53 diverge from each other in an upstream direction. As upstream displacement of the leaflets proceeds, although the ears 41a can move directly upstream in the upstream slots 51, the necessary simultaneous accompanying movement of the ears 41b in the oblique slots 53 causes pivoting of the leaflets to immediately begin, because the ears 41b in the slots 53 are being forced away from the centerline plane as they slid along the upstream sidewalls thereof while the sidewalls of the slots 51 which are parallel to the centerline plane restrain the ears 41a from essentially any movement but that in an axial direction.

As can be seen from FIGS. 2 and 3, the length of the oblique slots 53 is longer than the slots 51 which are parallel to the centerline. Accordingly, the ears 41b travel farther than do the ears 41a as the upstream movement continues, and this combined movement creates a form of a pivoting motion about the ears 41a, which themselves are also moving upstream in the valve body, with the result that pivoting of each leaflet toward its closed position promptly occurs. About the time the ears 41a reach the vicinity of the upstream ends of the slots 51 where they engage a short oblique sidewall section 55, see FIG. 3A, the flat surfaces of the mating edges 38 of the leaflets abut each other, and the cylindrical surface which forms the arcuate downstream edge 38a of each leaflet abuts the right circular cylindrical interior sidewall 47 of the valve body to provide a seal about the periphery of each leaflet in this region. The ears 41b preferably halt just short of the upstream ends of the slots 53 so that the closing force of the blood is borne by the ears 41a which engage the oblique sidewall sections 55 which are oriented at a downstream acute angle to the centerline plane, which angle is preferably about 2° to about 10°, and more preferably about 4° to about 8°, less than the angular inclination (see angle A in FIG. 3) of the leaflets in the closed position, and by the arcuate downstream edges. This arrangement creates a component or force vector that directs each leaflet toward the centerline and assures tight closing along the upstream mating edges 38.

Because the downstream ends of the angled slots 53 are open, the flow of blood therethrough to flush these regions is greatly facilitated, adding protection against potential clot formation. In addition, the slots 51 and 53 are located and proportioned so that, in the closed position illustrated in FIG. 3, neither the ears 41a nor the ears 41b reach the upstream end walls of the slots. More specifically, the short oblique flat sections 55 in the end wall regions at the upstream of the ends of the slots 51 physically prevent further upstream movement of the ears 41a, and when the two leaflets 33 abut along the mating edges 38 in the closed position, the length of the slots 53 is such that the ears 41b are located just short of the end walls at the upstream ends of the slots 53. As a result, when pressure is highest at the first instant of closure, there may be a short cleansing spurt of blood past each ear 41 and out the upstream edge of the respective slot depending upon the clearance between the facing flat wall sections at the time, which provides a further safeguard against clotting.

When normal blood flow resumes, downstream displacement of the leaflets 33 causes generally similar sliding-pivoting movement to be carried out in the reverse direction, this time guided by the sliding engagement of the ears 41b along the downstream edges of the oblique slots 53 while the ears 41a are again confined to movement in the parallel slots 51, wherein they now slide along the outer edges thereof, e.g. those located farther from the centerline plane. This pivoting action continues as the leaflets 33 move downstream within the valve body 32 from the closed position depicted in FIG. 3 to the open position depicted in FIG. 2 wherein the ears 41a are at the bottoms, and in contact with, the end walls of the slots 51 and wherein the ears 41b are near the open downstream ends of the slots 53. In this position, the flat short lateral edges 40 of the leaflets 33 likely abut each other, depending upon the tolerances of manufacture, and when such abutment occurs, the alignment of the major rectilinear surfaces of each leaflet body is precisely parallel to the centerline, as shown in FIG. 2.

Because the surfaces which define the main body portion of each leaflet 33 are oriented substantially parallel to the direction of blood flow in the open position, the leaflets 33 present minimal resistance to blood flow, and this feature, in combination with the elongated valve body having an axial length equal to greater than one-half the effective diameter of the passageway, creates a straightened, streamlined flow of blood through the valve, with a substantial reduction in turbulence and head loss as compared to comparable valves. By effective diameter of the valve passageway is meant the diameter of a right circular cylinder having the same cross-sectional area as the area of the passageway through the valve body 32. By centerline plane is meant the plane which passes through the centerline axis of the valve body passageway and which is perpendicular to the flat sidewall surfaces 49.

Depicted in FIGS. 6 through 11 is an alternative embodiment of a heart valve 61 also incorporating various features of the invention. The heart valve 61 has a valve body 63 generally similar to the valve body 32 described hereinbefore but having a different slot pattern. It has a similar exterior groove which accommodates a metal stiffening ring 64.

The valve body 63 is scalloped only at its downstream end where it has a depression or cutout region generally in the diametrically opposed regions where a pair of flat sidewall sections 65 appear in the otherwise cylindrical interior surface 67 of the valve body. The heart valve 61 employs a pair of leaflets 69 which can be identical to the leaflets 33 described hereinbefore, and which have mating edges 71 and arcuate edges 73. However, the slot pattern is such that the leaflets 69 are mounted with the reverse orientation, i.e. so that the mating edges 71 are located downstream in the open position and the arcuate edges 73 are located upstream.

With this orientation, the outflow surfaces of the leaflets are the convex surfaces 75, i.e. the surfaces which lie downstream in the closed position, and the inflow surfaces are the concave surfaces 77. Two pairs of relatively shallow slots 79, 81 are again provided in the flat sidewall region 65 of the valve body 63. The upstream slots 79 are straight, having generally parallel sidewalls, and are oriented parallel to the centerline of the valve passageway. The downstream slots 81 are also straight but are located at a downstream angle of about 35° to the centerline plane extending obliquely downstream from upstream ends located closer to the centerline plane than any portion of the upstream slots 79. The angular orientation can be varied somewhat, but the slot 81 is preferably aligned to form an angle of between about 45° and about 25° with the centerline plane.

The leaflets 69 similarly have a pair of ears 83a and 83b which protrude from lateral flat sections 85 along their opposite side edges, which ears are received in the slots 79, 81. Instead of being of spheroidal shape like the ears 41, the ears 83 have a generally cylindrical shape (see FIG. 10), and the slots 79, 81 are thus formed with more upright sidewalls that are aligned generally perpendicular to the valve body flat sidewall sections 65 to accommodate the ears and allow them to slide smoothly therewithin. As stated hereinbefore, the orientation and shape of the slot sidewalls is simply matched to the cross-sectional shape of the ears, with sufficient tolerance being provided so that binding cannot occur during the sliding translational motion of the ears within the slots.

Figure 6:
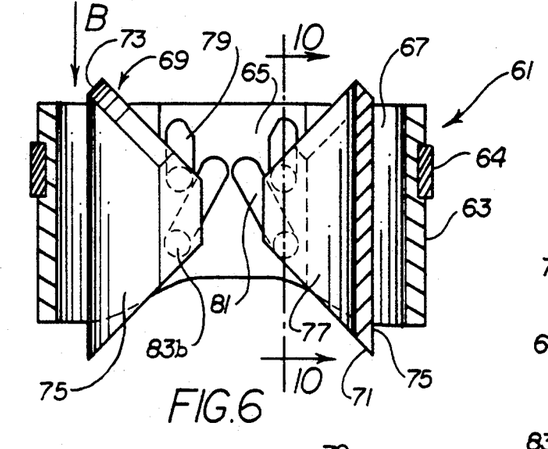
FIG. 6 is a view similar to FIG. 2 showing an alternative embodiment of a bi-leaflet heart valve embodying various features of the present invention with the occluders shown in the open position and with the left-hand occluder shown in elevation.

In the open position shown in FIG. 6, the leaflets 69 are oriented with their rectilinear cylindrical surfaces aligned parallel to the axial centerline through the valve body 63. This orientation and the smooth rectilinear surfaces of the interior of the valve body 63 provide minimum resistance to blood flow downstream through the passageway. This particular arrangement of curved leaflets provides a large central channel, which maximizes the central flow, along with a pair of side channels which still provide for substantial flow along the outflow surfaces 75 of the leaflets. If larger side flow channels are desired, either the leaflet mounting arrangement illustrated in FIGS. 1-5 is chosen, or cylindrical leaflets 69 having a more elliptical or oval shape are employed so as to thereby somewhat narrow the center flow channel and enlarge the side flow channels.

Figure 11:
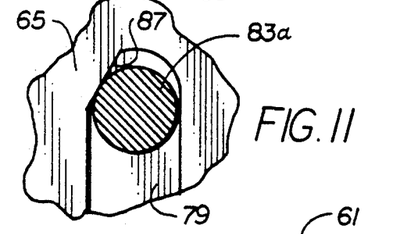
FIG. 11 is an enlarged partially sectional view showing the right-hand ear and slot arrangement in the valve orientation shown in FIG. 8.

As backflow of blood begins at the end of a pumping stroke, the drag of the upstream flowing blood on the inflow and outflow surfaces of the leaflets 69 causes the leaflets to be displaced in an upstream direction. The upstream ears 83a can only move in the slots 79 in a direction essentially parallel to the axis of the valve body, whereas the ears 83b slide obliquely along and in contact with the upstream sidewalls of the slots 81. The oblique slots are longer than the slots 79; and accordingly, the ears 83b travel farther than do the ears 83a as upstream translation continues. The combined movement of the ears 83 within the pair of slots creates a pivoting of each leaflet toward its closed position orientation, which promptly begins as soon as the ears 83 begin their movement in the slots 81. With respect to the right-hand leaflet shown in FIGS. 6, 7 and 8, such pivoting is in a clockwise direction about an axis defined by the coaxial upstream ears 83a, which axis continuously moves upstream until the ears 83a each abut an oblique end wall section 87 formed at the upstream end of each slot 79, as best seen in FIG. 11, and oriented at an upstream acute angle to the centerline plane and preferably an angle which is a few degrees greater than the angular inclination of the leaflets in the closed position, as generally explained hereinbefore. Similar to the case of the oblique end wall sections adjacent the upstream ends of the slots 51, the oblique end wall sections 87 provide the desired force vectors which assure that tight closing occurs. As in the case of the heart valve 31 described hereinbefore, the location of the oblique slots 81 is preferably such that the ears 83b are also at locations just slightly spaced from the upstream end walls of the slots in the closed position depicted in FIG. 8, thus again assuring that a cleansing spurt of blood flows through the region between the sidewalls and the bottom wall of the slots 79, 81 and the slightly undersized ears 83, as explained hereinbefore, and exits from the upstream ends of the slots at the instant of closing.

Figure 7:
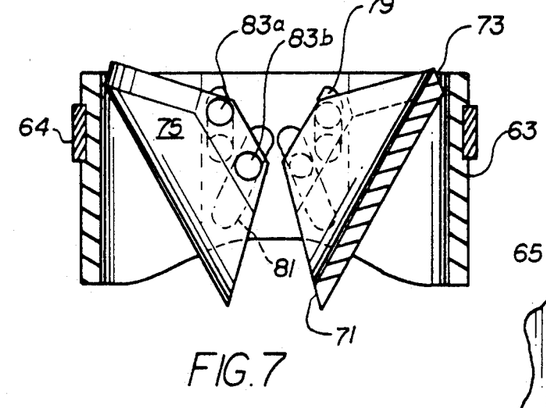
FIG. 7 is a view similar to FIG. 6 showing the occluders as they are moving upstream from the open position toward the closed position.
Figure 8:
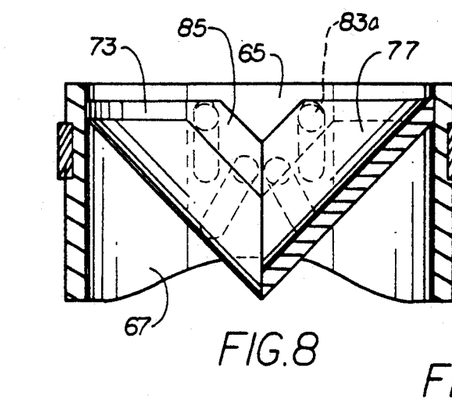
FIG. 8 is a view similar to FIGS. 6 and 7 showing the occluders after they have reached the closed position.
Figure 9:
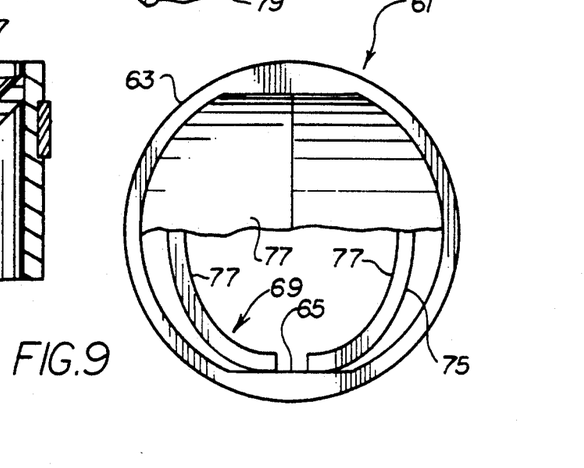
FIG. 9 is a plan view of the heart valve of FIGS. 6 and 8, with the occluders being shown in the open position in the lower half of the figure and in the closed position in the upper half.
Figure 10:
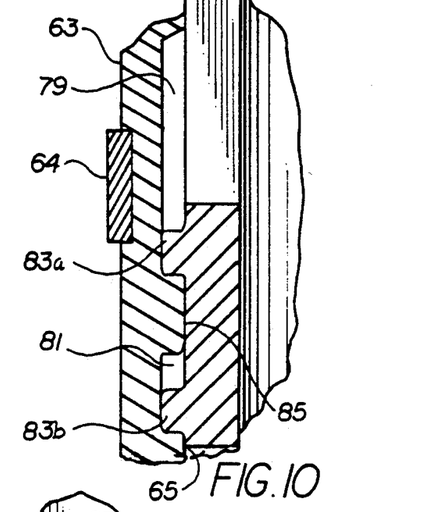
FIG. 10 is an enlarged fragmentary sectional view taken generally along the line 10—10 of FIG. 6.

As soon as normal blood flow resumes, downstream displacement of the leaflets 69 (from the position shown in FIG. 8) causes counterclockwise pivoting movement of the right-hand leaflet to occur, as can be seen by comparing FIG. 8 with FIG. 7. Both ears 83a and 83b move downward in the slots 79 and 81 with the pivoting again being about a downstream-sliding axis defined by the cylindrical ears 83a. The pivoting movement ceases when the ears 83a and 83b reach the bottoms and contact the downstream end walls of the slots 79 and 81, as best seen in FIG. 10. As indicated hereinbefore, in this open position, the alignment of the major rectilinear surfaces of each leaflet body is precisely parallel to the centerline, see FIG. 6. This open-position orientation is also depicted in the lower half of FIG. 9 which shows that the heart valve 61, which employs curved leaflets 69 arranged so that the outflow surfaces 75 are convex and the inflow surfaces 77 are concave, presents a generally larger central flow channel than a heart valve, such as the valve 31, wherein the curved leaflets are mounted with the opposite orientation. The closed position looking downward onto the concave inflow surfaces 77 is illustrated in the upper half of FIG. 9.

Figure 12:
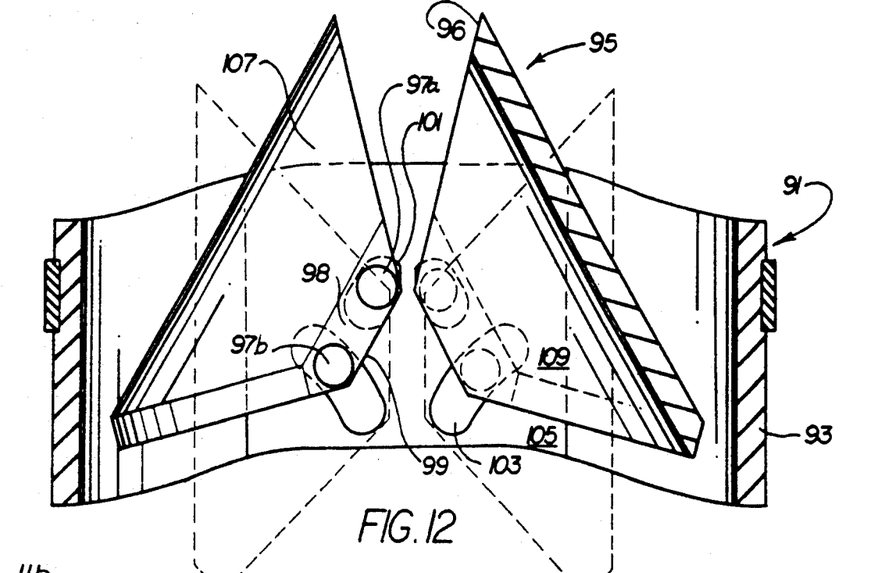
FIG. 12 is a view generally similar to FIG. 2 of another alternative embodiment of a heart valve incorporating various features of the invention which shows both leaflets in the position about midway from the open to the closed position in full lines and with the leaflets shown in the full open position in ghost outline.

Illustrated in FIG. 12 is still another embodiment of a heart valve 91, which fairly closely resembles the heart valve 32 depicted in FIG. 1. This valve illustrates that one of the slots need not be aligned parallel to the centerline, nor do the slots need to be straight. Heart valve 91 has a valve body 93 which is scalloped in a manner similar to the valve body 32 and employs a pair of leaflets 95 which are generally similar to the curved leaflets 33, having upstream mating edges 96. Each leaflet 95 has a pair of ears 97 which protrude from lateral flat surface sections 98 located adjacent lateral edge surfaces 99.

Pairs of slots 101, 103 are provided in the flat sidewall sections 105 of the valve body; the upstream slots 101 are straight and slightly angled with respect to the centerline plane, and the downstream slots 103 are arcuate and concave in a generally downstream direction, having sidewalls of generally similar curvature which are aligned with each other.

In FIG. 12, the leaflets 95 are shown in phantom outline in the open position wherein the convex inflow surfaces 107 and the concave outflow surfaces 109 are aligned parallel to the centerline, as in the case of the heart valve shown in FIGS. 1 through 5. When backflow of blood occurs following the end of each pumping stroke, the drag of the blood on the surfaces of the leaflets 95 causes them to again translate upstream. The upstream ears 97a of the pair move upward in the slightly angled slots 101 and therefore move slightly closer to the centerline plane. The downstream ears 97b slide upward in contact with the upstream concave arcuate edge of the downstream slots 103 and cause the right-hand leaflet 95 to immediately begin to pivot in a counterclockwise direction about an axis defined by the coaxial upstream cylindrical ears 97a. The pivot axis of course is continuously changing as the ears 97a slide upstream toward the upstream ends of the slots 101. FIG. 12 depicts the leaflets in an intermediate closing position where there is contact between the ears 97a and the upstream sidewalls of the slots 101 and also contact between the ears 97b and the concave upstream sidewalls of the slots 103. Following complete closing of the leaflets 95, opening movement of the leaflets 95 occurs on the next pumping stroke of the heart with the ears 97a, 97b sliding downward in the slots 101, 103 in contact with the downstream edges thereof.

Figure 13:
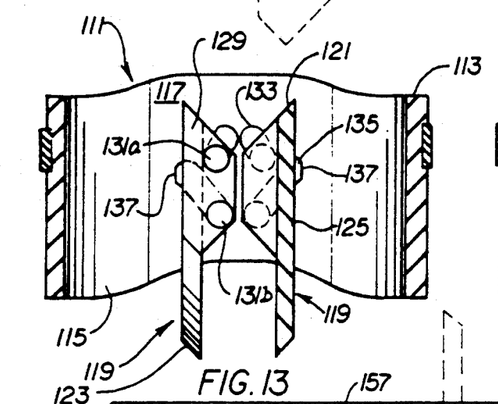
FIG. 13 is a view similar to FIG. 2 of yet another heart valve embodying various features of the invention wherein flat plates constitute the major portions of the occluders with the occluders being shown in the open position and the left-hand occluder being shown in elevation.
Figure 14:
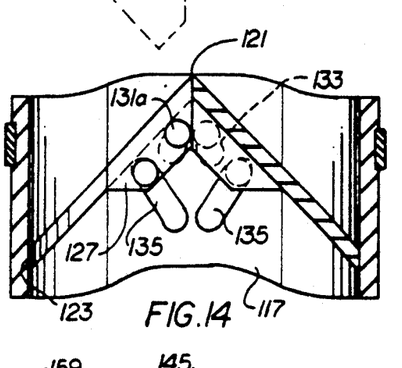
FIG. 14 is a view of the valve of FIG. 13, but showing the occluders in the closed position.

Depicted in FIGS. 13 and 14 is a valve 111 generally similar to that shown in FIG. 1 which utilizes a pair of leaflets in the form of flat plates. The heart valve 111 has a valve body 113 that is scalloped both along its upstream and downstream edges similar to the valve body 32. It has a generally cylindrical interior wall 115 that is interrupted at diametrically opposite locations to provide a pair of flat interior wall sections 117 wherein slot patterns are provided for mounting a pair of leaflets 119. Again, for purposes of illustration, the left-hand leaflet is shown in elevation whereas the right-hand leaflet is shown in section as in the case of the heart valves previously described herein. Each of the leaflets has a flat upstream mating edge 121 and an arcuate downstream edge 123. The leaflets have main body portions 125 in the form of flat plate portions of uniform thickness and have side extensions 127 having a thickness about twice that of the main body portions. The lateral surfaces of the side extensions are flat surfaces 129 from which a pair of ears 131a and 131b protrude. The ears 131 are received in pairs of slots 133, 135 provided in the flat interior wall sections 117 of the valve body.

In the open position illustrated in FIG. 13, the flat main body portions 125 of the leaflets are oriented parallel to the centerline through the valve, and thus the major inflow and outflow surfaces of each of the leaflets 119 is precisely parallel to the centerline plane, i.e. the plane which contains the centerline of the valve passageway and is perpendicular to the pair of diametrically opposed flat sidewall portions 117. This arrangement creates three approximately equal flow passageways through the valve 111 so there is very substantial blood flow adjacent both the outflow and inflow surfaces of each leaflet. In this position, the ears 131a and 131b are located at the downstream ends of the respective slots 133, 135. As the backflow of blood begins at the end of a pumping stroke, the drag of the upstream flowing blood on the inflow and outflow surfaces of the leaflets 119 causes the leaflets to be displaced in an upstream direction. The ears 131 move upward in the slots 133, 135, again causing pivoting of the leaflets to occur about the coaxial upstream ears 131a which are themselves sliding upward against the upstream sidewalls of the slots 133. The upstream slots are oriented at a downstream angle of about 35° and thus the ears 131a move closer to the centerline plane as the closing pivoting movement continues. The downstream slots 135 are oriented at an upstream angle of about 45° to the centerline plane and are longer in length than the upstream slots 133, resulting in a combined pivoting or rotational movement of the leaflets toward the closed position orientation depicted in FIG. 14.

In FIG. 14, where the completely closed position is illustrated, the mating surfaces 121, which are located at the upstream edges of each of the two leaflets 119, are in contact with each other. The side extensions 127 of the leaflets have their upstream ends contoured so as to be extensions of the mating edges 121, and thus they can also abut each other. At the same time, the downstream arcuate edges 123 of the leaflets are seated against the cylindrical sections 115 of the interior wall of the valve body, thus providing a good seal at these locations. Preferably, the upstream end wall of each slot 135 is provided with an oblique short flat surface 137 which creates an overall force vector that assures tight closing at the upstream mating edges 121. In the closed position, the ears 131a will be at or closely adjacent the upstream ends of the slots 133. When normal downstream blood flow resumes at the beginning of the next pumping stroke, the ears 131 translate downstream in the slots 133, 135, sliding in engagement generally along the downstream sidewalls until they reach the bottom thereof and causing pivoting of the leaflets to the open position shown in FIG. 13.

Figures 15, 16:
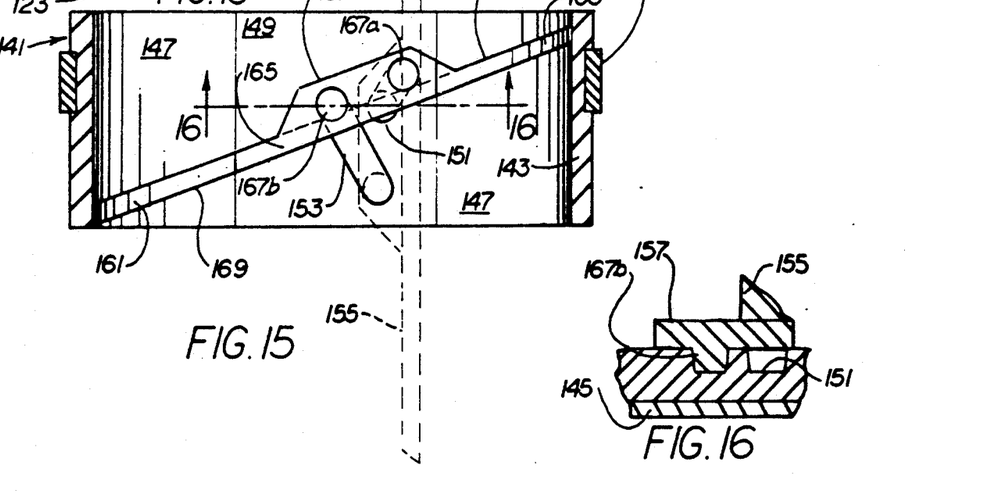
FIG. 15 is a view of still another heart valve embodying various features of the invention employing only a single occluder which is shown in full lines in the closed position and in ghost outline in the open position.
FIG. 16 is a fragmentary sectional view of the heart valve of FIG. 15 taken generally along the line 16—16 of FIG. 15.

Depicted in FIG. 15 is a heart valve 141 generally similar to that shown in FIGS. 13 and 14 but utilizing only a single occluder. More specifically, the heart valve 141 has a valve body 143 which has a right circular cylindrical exterior surface in which a groove is provided to accommodate a stiffening ring 145. The interior surface 147 is also cylindrical except for a pair of generally diametrically opposed interior flat wall sections 149 wherein a set of guiding slots is located in the form of a pair of slots 151, 153 in each flat wall section.

A single occluder 155, shown in elevation, includes a main body in the form of a flat plate having a pair of side extensions 157 which extend upstream from the inflow surface 159 of the occluder in the closed position. The occluder 155 has an arcuate downstream edge surface 161 and an arcuate upstream edge surface 163, both of which seal against the cylindrical interior surface 147 of the valve body, and it has a pair of parallel flat lateral edge surfaces 165 located between such arcuate edge surfaces which extend upward along the lateral edges of the side extensions 157. A pair of ears 167 protrude laterally from each lateral edge surface 165. The upstream ear 167a is received in the upstream slot 151, which is the shorter of the two slots, and the ear 167b is received in the slot 153. As best seen in FIG. 16, the ears are generally frustoconical in shape, and the slots have a corresponding cross-section of slightly larger dimension to accommodate the sliding movement of the ears therewithin.

The occluder 155 is shown in phantom outline in the open position in FIG. 15. As the backflow of blood begins at the end of a pumping stroke, the drag of the blood in an upstream direction, i.e. upward in FIG. 15, causes the occluder to be displaced upstream. Because of the diverging orientation of the slots 151, 153, the ear 167a in the upstream slot 151 moves upstream and to the right (as viewed in FIG. 15), and the ear 167b in the downstream slot 153 moves upstream and to the left. Generally, as hereinbefore explained, pivoting closing movement occurs about the axis defined by the two upstream ears, i.e. the ears 167a, which axis is shifting upstream as pivoting occurs, and the slot 153 is proportioned to require a translational movement about twice as long as the translational movement within the slot 151. As a result, there is pivoting of the occluder 155 in the clockwise direction (again as viewed in FIG. 15) of an angular amount of about 70°. During this pivoting movement, the ears 167 slide in contact with the upstream sidewalls of the slots 151, 153 which guide the closing movement. It can be seen that the diverging relative movement of the two ears 167, which results from the upstream drag forces on the flat inflow surface 159 and the flat outflow surface 169 of the occluder, causes pivoting to immediately begin. As pivoting continues, the outflow surface 169 becomes more directly impinged by the backflowing blood, thus increasing the rate of angular rotation of the occluder to assure prompt closing occurs.

In the closed position depicted in full lines in FIG. 15, the upstream angular edge surface 163 and the downstream angular edge surface 161 seal against the cylindrical wall sections 147 of the interior of the valve body, and the flat lateral surfaces 165 fit closely adjacent the flat interior walls 149 of the valve body and permit only controlled leakage therepast. Each ear 167a will usually locate closely adjacent or in contact with the upstream end wall of the slots 151; however, the location of the slot 153 is preferably such that the ears 167b do not reach the upstream ends thereof. When the next pumping stroke begins, the ears 167 translate downward in the slots 151, 153, and rotation of the occluder 155 in a counterclockwise direction (as viewed in FIG. 15) occurs until the occluder reaches the parallel orientation shown in phantom outline in FIG. 15. The proportioning and the locations of the ears 167 and the slots 151, 153 is preferably such that both ears are in contact with the bottoms of the slots; in any event, at least one is in contact with a downstream end wall with the other being very closely adjacent thereto.

In summary, it can be seen that the invention provides simple and straightforward arrangements for obtaining the advantage of having one or more occluders able to assume a precisely parallel orientation in the open position which decreases resistance to blood flow through a prosthetic valve and thus directly addresses concerns to which more attention has recently been given in the field of prosthetic heart valves. Moreover, the reliability of these valve constructions should be evident, and because of their relative simplicity, manufacturing difficulties are greatly reduced.

Although the invention has been described with respect to a number of preferred embodiments, which include the best mode believed by the inventors to achieve these objectives in prosthetic valves, it should be understood that various changes and modifications as would be obvious to one having the ordinary skill in this art may be made without departing from the scope of the invention which is defined by the claims appended hereto.

Particular features of these heart valves are emphasized in the claims which follow.

What is claimed is:

1. A prosthetic heart valve which comprises
   a generally annular valve body having an interior sidewall which defines a central passageway therethrough, for the passage of blood in a downstream direction, having a centerline extending in the direction of blood flow, said sidewall having a pair of diametrically opposed flat sections,
   occluder means having an inflow surface and an outflow surface and at least one downstream edge, which is mounted in said valve body to alternately permit the flow of blood therethrough in a downstream direction when in an open position and block the flow of blood in the reverse direction when in a closed position,
   said valve body and said occluder means having a pivot arrangement by which said occluder means is guided in moving between said open position and said closed position,
   said pivot arrangement including first and second elongated slots located in each of said opposed flat sections of said valve body sidewall, said first and second elongated slots being oriented at different angles with respect to said centerline, and also including first and second ear means protruding from a flat lateral surface on each side of said occluder means, which ear means are respectively received within said first and second slots, and
   said slots being positioned so that, when backflow of blood through said valve body causes said occluder means to translate upstream, said first and second ear means engage sidewalls of said first and second slots in such manner that said occluder means quickly begins to pivot and is thereafter guided in its movement to the closed position.

2. A prosthetic heart valve according to claim 1 wherein said sidewalls of each of said elongated slots are substantially straight and parallel.

3. A prosthetic heart valve according to claim 2 wherein said slots are positioned so that, when said occluder means is in the open position, major portions of said inflow and outflow surfaces lie substantially parallel to said valve body centerline.

4. A prosthetic heart valve according to claim 3 wherein said substantially straight sidewalls of said first slots extend in a direction substantially parallel to the centerline of said central passageway.

5. A prosthetic heart valve according to claim 4 wherein said substantially straight sidewalls of said second slots having upstream ends are oriented at an upstream-facing angle of between about 25° and about 50° to the centerline plane of said valve body.

6. A prosthetic heart valve according to claim 4 wherein said occluder means includes a pair of mating occluders and wherein said first and second slots are located so that, when said occluders move from the open position to the closed position, the downstream edges of said occluders move inward toward the centerline plane.

7. A prosthetic heart valve according to claim 6 wherein two pairs of said elongated slots are provided to guide each said occluder and wherein said second slots are located such that the upstream ends thereof are located between the downstream ends of said first slots and the centerline plane and such that said second slots extend in a downstream direction away from said centerline plane.

8. A prosthetic heart valve according to claim 4 wherein said occluder means includes a pair of mating occluders and wherein said first and second slots are located so that, when said occluders move from the open position to the closed position, the downstream edges of said occluders move outward away from the centerline plane.

9. A prosthetic heart valve according to claim 8 wherein two pairs of said elongated slots are provided to guide each occluder and are located in said flat sidewall surfaces such that said second slot of each said pair extends from a downstream location, generally axially aligned with said first slot, in an upstream direction away from said centerline plane.

10. A prosthetic heart valve according to claim 1 wherein said occluder means includes a pair of mating occluders each having a main body portion in the form of a section of a hollow cylinder.

11. A prosthetic heart valve according to claim 1 wherein said occluder means includes a pair of mating occluders each of which has a main body section that is substantially flat.

12. A prosthetic heart valve which comprises
a generally annular valve body having an interior generally cylindrical sidewall which defines a central passageway, for the passage of blood therethrough in a downstream direction, having a centerline extending in the direction of blood flow, said sidewall having a pair of diametrically opposed flat sections, whereby a plane perpendicular to said flat sections and containing said centerline is referred to as the centerline plane,
a pair of substantially identical occluders each having an inflow surface, an outflow surface and a pair of substantially flat lateral surfaces, which occluders are mounted in said valve body to alternately permit the flow of blood therethrough in a downstream direction when in an open position and block a flow of blood in the reverse direction when in the closed position,
said valve body and said occluders having a pivot arrangement by which said occluders are guided along translating-pivoting paths in moving between said open position and said closed position,
said pivot arrangement including a set of slots having upstream ends and downstream ends for each said occluder and also including ear means protruding from each said lateral surface of each said occluder, each set having two pairs of first and second elongated slots with one pair being located in each of said opposed flat sections of said valve body sidewall and each said ear means including two separate ears which are respectively received within a pair of said slots, and said slots being positioned so that, when each said occluder is displaced upstream from its open position by the backflow of blood, said ears engage and slide against sidewalls of said first and second slots so that each said occluder quickly begins to pivot toward its closed position orientation as it translates upstream guided in movement by the orientation of said pairs of slots.

13. A prosthetic heart valve according to claim 12 wherein at least one of said elongated slots of each said pair of slots is oriented at an angle of at least about 30° to said centerline plane.

14. A prosthetic heart valve according to claim 13 wherein the other of said slots has substantially straight sidewall sections which are substantially parallel to said centerline plane.

15. A prosthetic heart valve according to claim 12 wherein at least one of said elongated slots of each pair of slots is curved so that said ears which are received therein slide along arcuate paths as said occluder moves from the open to the closed position.

16. A prosthetic heart valve according to claim 15 wherein each said arcuate path is concave in the downstream direction.

17. A prosthetic heart valve according to claim 12 wherein said ears have surfaces curved in a plane parallel to said lateral surface of said occluder, wherein the upstream end sections of said first slots are located upstream of the upstream end sections of said second slots and are each formed with a flat end wall section that is oblique to said sidewalls of said slot, and wherein said first slots are located so that said ear that is received therewithin bears against said oblique end wall section when said occluder is in its closed position.

18. A prosthetic heart valve according to claim 12 wherein said occluders have major body portions of which the outflow and inflow surfaces are rectilinear and wherein said sets of slots are positioned so that said rectilinear occluder surfaces can assume an orientation parallel to said centerline when said occluders are in the open position.

19. A prosthetic heart valve which comprises
a generally annular valve body having an interior sidewall which defines a central passageway therethrough, for the passage of blood in a downstream direction, having a centerline extending in the direction of blood flow, said sidewall having a pair of diametrically opposed flat sections,
occluder means having a rectilinear inflow surface and a rectilinear outflow surface, which is mounted in said valve body to alternately permit the flow of blood therethrough in a downstream direction when in an open position and block the flow of blood in the reverse direction when in a closed position;
said valve body and said occluder means having a pivot arrangement by which said occluder means is guided in moving between said open position and said closed position, which pivot arrangement includes first and second elongated slots located in each of said opposed flat sections of said valve body sidewall and also includes first and second ear means protruding from a flat lateral surface on each side of said occluder means, which first and second ear means are respectively received within said first and second slots,
said slots being positioned so that said rectilinear inflow and outflow surfaces can assume an orientation parallel to said centerline when said occluder means is in the open position, and said slots being positioned and aligned so that, when backflow of blood through said valve body causes said occluder means to translate upstream, said first and second ear means engage sidewalls of said first and second slots in such manner that said occluder means quickly begins to pivot toward its closed position orientation.

20. A prosthetic heart valve according to claim 19 wherein said occluder means includes two identical leaflets.

* * * * *